(12) United States Patent
McConnell

(10) Patent No.: US 9,521,788 B2
(45) Date of Patent: Dec. 13, 2016

(54) MOBILE DEVICE COVER WITH DETACHABLE EMF BLOCKER

(71) Applicant: Prince Lionheart, Inc., Santa Maria, CA (US)

(72) Inventor: Kelly McConnell, Santa Ynez, CA (US)

(73) Assignee: Prince Lionheart, Inc., Santa Maria, CA (US)

(*) Notice: Subject to any disclaimer, the term of this patent is extended or adjusted under 35 U.S.C. 154(b) by 135 days.

(21) Appl. No.: 14/457,081

(22) Filed: Aug. 11, 2014

(65) Prior Publication Data

US 2015/0043163 A1    Feb. 12, 2015

Related U.S. Application Data

(60) Provisional application No. 61/864,493, filed on Aug. 9, 2013.

(51) Int. Cl.
| | | |
|---|---|---|
| *H05K 9/00* | (2006.01) | |
| *A41D 31/00* | (2006.01) | |
| *A61N 1/16* | (2006.01) | |
| *A61N 1/08* | (2006.01) | |

(52) U.S. Cl.
CPC .............. *H05K 9/00* (2013.01); *A41D 31/0011* (2013.01); *A61N 1/08* (2013.01); *A61N 1/16* (2013.01)

(58) Field of Classification Search
CPC combination set(s) only.
See application file for complete search history.

(56) References Cited

U.S. PATENT DOCUMENTS

| | | | | |
|---|---|---|---|---|
| 2,404,225 A * | 7/1946 | Green | ..................... | A41D 13/04 2/457 |
| 4,441,025 A * | 4/1984 | McCoy, Jr. | ................ | G21F 3/03 2/2.5 |
| 4,924,103 A * | 5/1990 | Stein | ......................... | G21F 3/03 2/411 |
| 5,103,504 A * | 4/1992 | Dordevic | .............. | A41D 13/008 139/425 R |
| 5,621,188 A * | 4/1997 | Lee | .......................... | A61N 1/14 174/390 |
| 5,745,925 A * | 5/1998 | Ghilardi | ..................... | G21F 3/02 2/338 |
| 5,968,854 A * | 10/1999 | Akopian | ............. | A41D 31/0066 428/357 |
| 6,783,839 B1 * | 8/2004 | Alpini | .................. | A41D 13/008 2/102 |
| 7,161,164 B2 * | 1/2007 | Glukhovsky | .............. | A41F 9/00 2/455 |
| 7,772,504 B1 | 8/2010 | Tashjian | | |

(Continued)

*Primary Examiner* — Lisa Lea Edmonds
(74) *Attorney, Agent, or Firm* — WPAT, P.C., Intellectual Property Attorneys; Anthony King

(57) ABSTRACT

An EMF blocker having a blocking shield made of a material to sufficiently block EMF radiation emitted from electronic devices. The EMF blocker has necessary coupling mechanism to detachably couple to the electronic device so that an ideal relative positioning between the electronic device and the EMF blocker is ensured. The EMF blocker also has necessary coupling mechanism to couple to a user of the electronic device to the EMF blocker. The EMF blocker can be in the form of a bib, an apron, a blanket, an article of clothing, a panel. The electronic device can be any mobile electronic device, laptop computer, or even a desktop computer.

10 Claims, 14 Drawing Sheets

(56) References Cited

U.S. PATENT DOCUMENTS

| | | | |
|---|---|---|---|
| 8,205,744 B1 | 6/2012 | Tashjian | |
| 8,434,169 B2 | 5/2013 | Maner | |
| 9,224,508 B2* | 12/2015 | Reynolds | A41B 3/02 |
| 2003/0224684 A1* | 12/2003 | Botturi | A41D 31/0011 |
| | | | 442/187 |
| 2005/0028240 A1* | 2/2005 | Brennan | A41D 13/00 |
| | | | 2/69 |
| 2009/0114857 A1* | 5/2009 | DeMeo | G01V 5/0008 |
| | | | 250/516.1 |
| 2010/0210161 A1* | 8/2010 | Jensen | D06M 11/53 |
| | | | 442/132 |
| 2012/0114270 A1* | 5/2012 | Roberts | A45C 11/00 |
| | | | 383/109 |
| 2012/0185999 A1 | 7/2012 | Raviv | |
| 2012/0186000 A1* | 7/2012 | Raviv | A41D 27/205 |
| | | | 2/247 |
| 2014/0051480 A1* | 2/2014 | Cruz | H04B 1/3838 |
| | | | 455/566 |
| 2014/0177196 A1* | 6/2014 | Kumar | H04B 1/3838 |
| | | | 361/816 |
| 2014/0220845 A1* | 8/2014 | Elder | B32B 5/08 |
| | | | 442/198 |
| 2014/0246609 A1* | 9/2014 | DeBaun | G21F 1/125 |
| | | | 250/515.1 |
| 2016/0044841 A1* | 2/2016 | Chamberlain | A61N 1/3718 |
| | | | 174/350 |

* cited by examiner

MOBILE DEVICE COVER WITH DETACHABLE EMF BLOCKER

CROSS-REFERENCE TO RELATED APPLICATION

This application claims priority to U.S. provisional application No. 61/864,493 dated Aug. 9, 2013 entitled "Mobile Device Cover with Detachable EMF Blocker" the contents of which is hereby incorporated by reference.

BACKGROUND OF THE INVENTION (1) Field of the Invention

The field of the invention is accessories for mobile electronics.

(2) Description of Related Art Including Information Disclosed Under 37 CFR 1.97 and 1.98

Electronic devices such as desktop computers, cellular phones, laptop computers, tablet PCs such as iPads®, portable gaming devices, portable DVD players, wireless keyboards, are known to emit electromagnetic field (EMF) radiation that are hazardous to people in close proximity.

It is known to reduce exposure to radiation by wearing a lead shielding such as a lead apron or a lead vest. Such solution is currently used by medical personnel who are frequently exposed to radiation. There is no currently suitable solution, however, for the general public to minimize one's exposure to EMF created by these mobile personal electronics while at the same time keeping such mobile electronics in an ideal relative position, relative to the user and the wearable shielding. More specifically, there is an urgent need for feasible solutions that minimize exposure of EMF in young active children who play with such mobile electronics, and may be difficult to keep any type of shielding in place to protect them.

Since 2007 scientists have been warning the public about the steady increase in EMF radiation due to the popularity of mobile devices, laptops, iPads®, and tablets. Now the number of personal electronic devices has skyrocketed and EMF radiation is everywhere. Specifically, the Bio Initiative Working Group consisting of twenty-nine independent scientific groups from all over the world recently reviewed and compared data on over 1800 studies on EMF radiation. The group concluded that electromagnetic radiation damages DNA, interferes with DNA repair, and creates greater toxicity in the genes. The group also cites studies showing pathological leakage of the blood-brain barrier and altered immune function. There are also dozens of studies linking cell phones on standby carried on a belt or in a pocket of men and wireless laptops to sperm damage: quality, mobility & death, all affecting fertility and reproduction. Perhaps even more alarming is the evidence of increased incidence of child and adult brain tumor risks that is linked to electromagnetic radiation. Also the use of mobile & cordless phones is reported to increase the incidence of acoustic neuroma. EMF exposure has been further correlated with other cancers, such as child and adult leukemia and breast cancer in both men and women. The report also cites studies showing a link between electromagnetic radiation and neurological diseases, such as Alzheimer's & ALS, miscarriage and a number of cardiovascular effects. Taken altogether the reports ring the alarm bell that both children and adults have increased health risks from EMF and there is a concrete need to protect humans from such exposure.

United States patent application publication number 20120185999 by Ravin discloses a pouch in pants for an electronic device, the pants pocket having electromagnetic shielding. Ravin was concerned with securing the electronic device in a position where a user would be protected when the device is in the pants pocket.

U.S. Pat. No. 8,434,169 issued to Maner discloses a shielding or protective garments for protecting women from electromagnetic fields. Maner was more specifically concerned with protecting and/or reducing exposure of reproductive organs and fetuses of women to electromagnetic fields.

U.S. Pat. No. 8,205,744 issued to Tashjian discloses a protective laptop carrier. Tashjian was concerned with shielding a laptop user from the harmful heat and the EMF generated including but not limited to RF microwave radiation emitted by a laptop particularly when being used on the user's chest or lap regions. The shielding also serves as a lightweight carrying case and base support for the laptop computer.

All referenced patents, applications and literatures are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. The invention may seek to satisfy one or more of the above-mentioned desires. Although the present invention may obviate one or more of the above-mentioned desires, it should be understood that some aspects of the invention might not necessarily obviate them.

BRIEF SUMMARY OF THE INVENTION

As described above and shown in the drawing figures, the invention is about having an EMF blocker being an electronic device accessory, or as part of an electronic device accessory. The EMF blocker includes a blocking shield that can be made of various materials known to block EMF radiation. This general idea of using an EMF blocker can apply to cellular phone cases, laptop covers, laptop pillow desks, laptop portable tables, desktop computers, all other tablet computers and electronic reading devices. Many of the accessories to these personal electronics can have an EMF blocker coupled to it, so that a user is more likely to remember to use the EMF blocker over his/her body while using the electronics device.

DETAILED DESCRIPTION OF THE INVENTION

Figure 1:
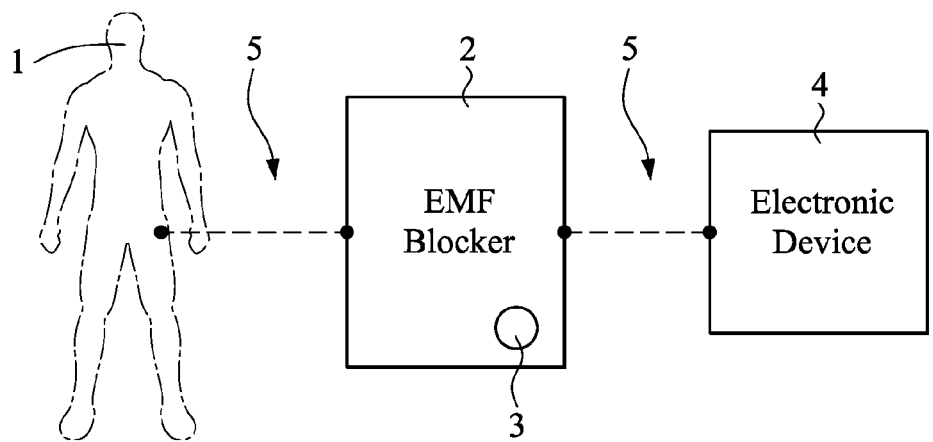
FIG. 1 shows an EMF blocker with a blocking shield incorporated therein, and the EMF blocker is coupled to a user and an electronic device.

Referring now to the drawings wherein the showings are for purposes of illustrating a preferred embodiment of the present invention and not for purposes of limiting the same, a first embodiment of the invention is Mobile Device Cover with Detachable EMF Blocker illustrated in FIG. 1, the invention includes a blocking shield 3 and coupling means 5 to a user and an electronic device 4. An EMF blocker 2 with a blocking shield 3 is detachably coupled to an electronic device 4 by generally known methods. The inventor has surprisingly discovered the importance of tethering the electronic device 4 to the EMF blocker 2. When the EMF blocker 2 is tethered, or coupled, to the electronic device 4, a relative position between the electronic device 4 and the EMF blocker 2 is ensured. Further, there has been no attempt in the art to make an EMF blocker 2 as part of an accessory to the electronic device 4 while also coupling the EMF blocker 2 to a user. This is an important distinction because while in some forms may limit a user's freedom of movement, it ensures maximum blockage of EMF radiation to a user, especially toddler and children who are more likely to forget to use the EMF blocker 2, or are too active to keep the EMF blocker 2 in place. By having an EMF blocker 2 that tethers an electronic device 4 to a child-aged user, a parent can easily enforce and monitor proper usage of the EMF blocker 2.

Figure 2:
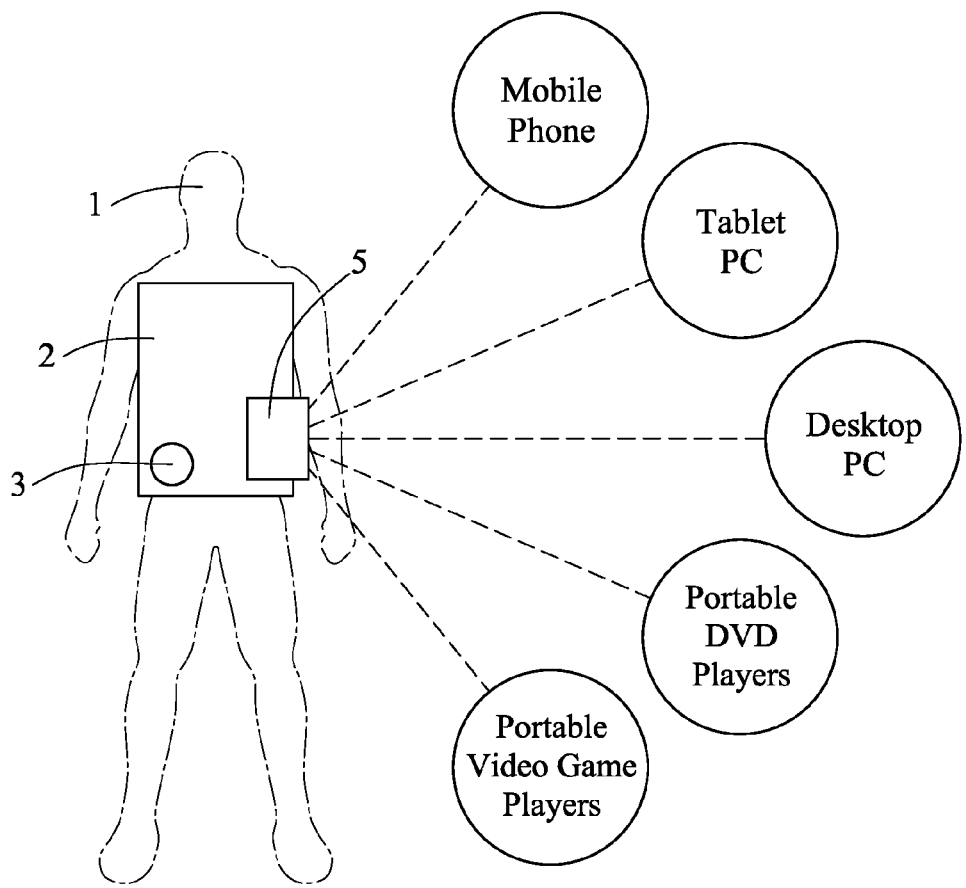
FIG. 2 illustrates the EMF blocker and blocking shield coupled to different types of electronic devices via a coupling mechanism.

FIG. 2 shows a user with an EMF blocker 2 and a coupling mechanism 5 capable of attaching to a mobile phone, tablet personal computer, desktop personal computer, keyboard, portable DVD player, and portable video game player. As will be discussed later, many coupling methods are contemplated.

Figure 3A:
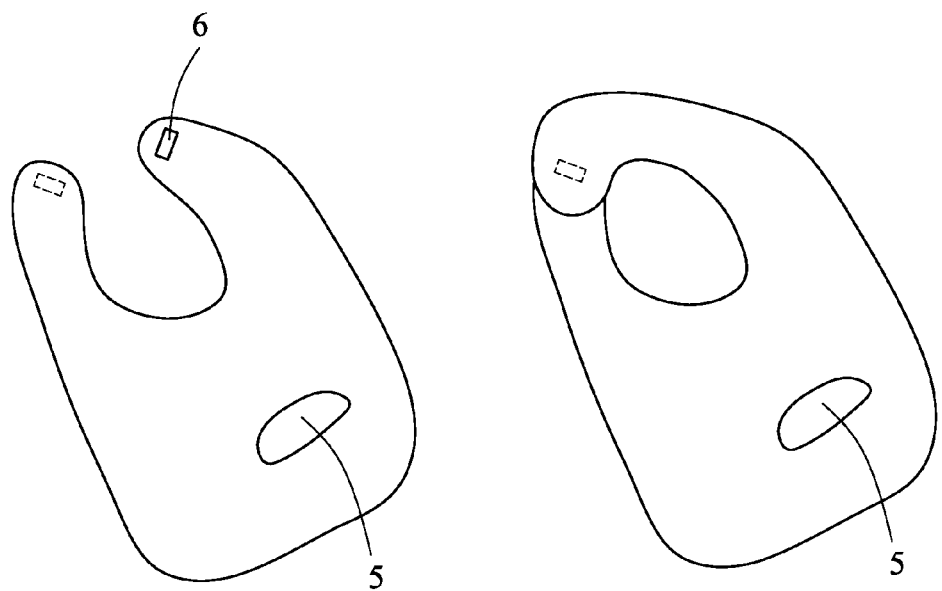
FIG. 3A shows two EMF blockers in the form of a bib, each having some kind of coupling mechanism to couple to the electronic device.

FIG. 3A shows an EMF blocker 2 in the form of a bib with a loop design and two flaps 12 for attaching around a user's neck. The fastening mechanism 6 could be hook and loop, magnets, or similar known quick releasable attachment designs. Further the flap 12 portion could be weighted. The additional weight would help maintain a user's center of gravity by balancing against the weight of the electronic device 4 and aid in posture. A further coupling mechanism 5 is integrated into the bib design for attachment to an electronic device 4.

Figure 3B:
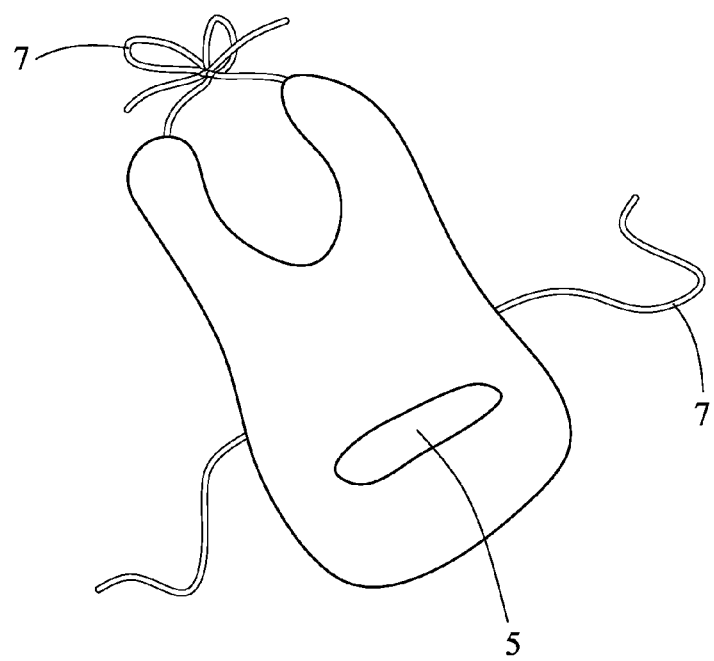
FIG. 3B shows an EMF blocker in the form of an apron with straps, having some kind of coupling mechanism to couple to the electronic device.

FIG. 3B shows an EMF blocker 2 in the form of an apron with straps 7. The straps 7 can be attached at a lower or medial portion of an EMF blocker 2 for tying around a user's torso and straps 7 at an upper portion of an EMF blocker 2 for tying around a user's neck. This would help stabilize the EMF blocker 2.

Figure 3C:
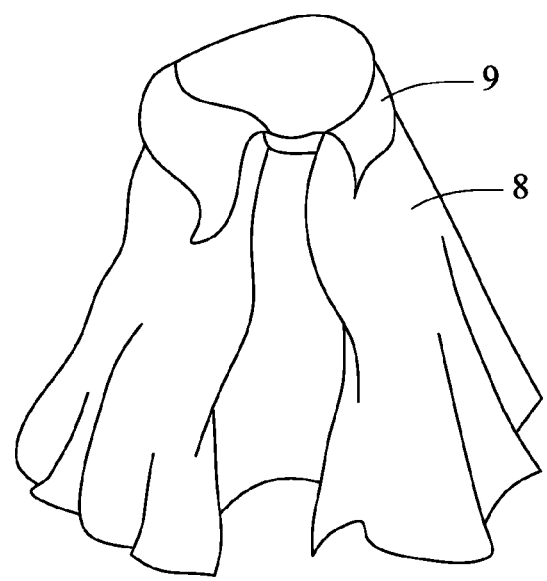
FIG. 3C shows an EMF blocker in the form of a cape with a collar.

FIG. 3C shows an EMF blocker 2 in the form of a cape 8 with a collar 9. The cape 8 could be affixed with a button or snap. Shielding the throat and neck is important because it is believed that throat and thyroid cancers are on the rise due to increased exposure to EMF radiation.

Figure 3D:
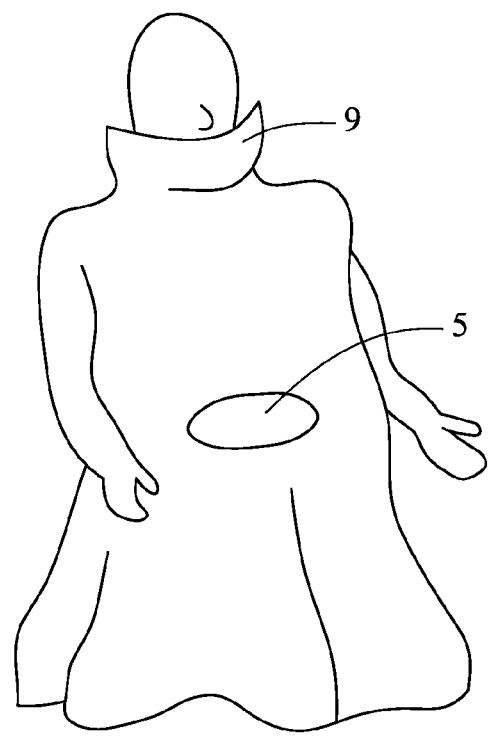
FIG. 3D shows an EMF blocker in the form of a cape with a collar/neck guard on a user, the cape having some kind of coupling mechanism to couple to the electronic device.

FIG. 3D shows an EMF blocker 2 in the form of a cape 8 with a collar 9 on a user. In this embodiment the user puts on a cape 8 in a reverse orientation thus leaving a collar 9 in front of the neck and face. Additionally, the cape 8 can be designed with sleeves or with sleeve holes for the user's arms.

Figure 3E:
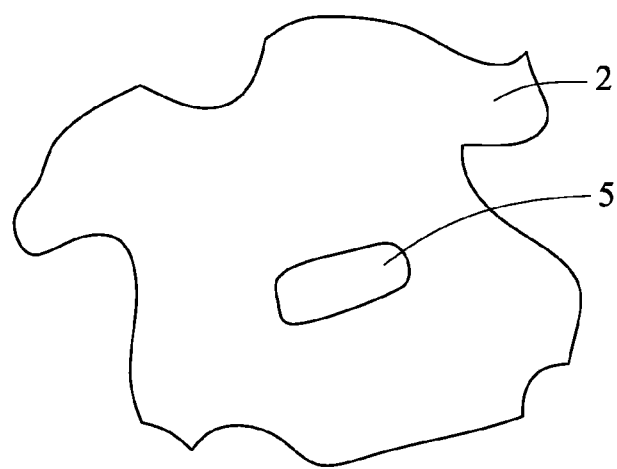
FIG. 3E shows an EMF blocker in the form of an odd shaped panel, having some kind of coupling mechanism to couple to the electronic device.

FIG. 3E shows an EMF blocker 2 in the form of an odd shaped panel. There is no requirement that the EMF blocker 2 be symmetric in shape. Further, the position of the coupling mechanism 5 for an electronic device 4 can be placed in different spots to suit different user's requirements. Here in FIG. 3E, the panel is generally soft and pliable.

Figure 3F:
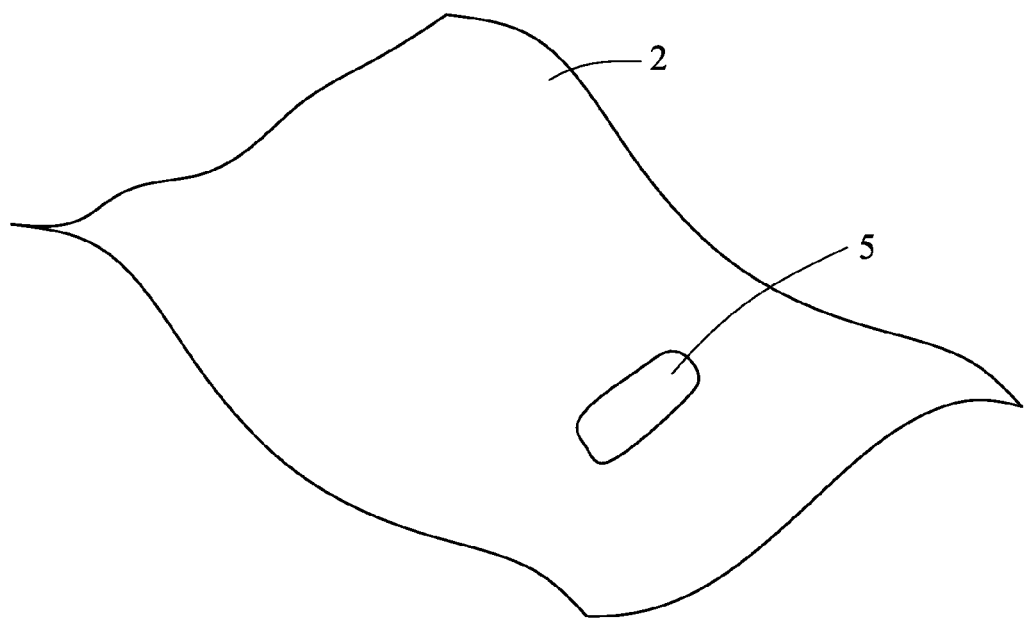
FIG. 3F shows an EMF blocker in the form of a blanket, having some kind of coupling mechanism to couple to the electronic device.

FIG. 3F shows an EMF blocker 2 in the form of a blanket. The coupling mechanism 5 could be in the form of a pocket or other attachment means. The position of the coupling mechanism 5 for an electronic device 4 could be in a medial portion so that the blanket could cover the upper and lower torso of a user.

Figure 3G:
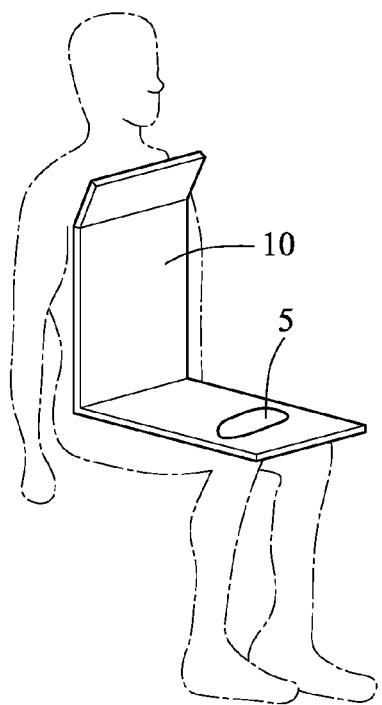
FIG. 3G shows an EMF blocker in the form of a hard or semi-rigid panel, having some kind of coupling mechanism to couple to the electronic device.

FIG. 3G shows an EMF blocker 2 in the form of a hard panel 10. The panels can fold over to reduce the overall space taken up for transport or when not in use. The hard panel 10 could be used for protection of an electronics device as well as formed for storage of the device. It should be understood that the panel could alternatively be made of soft materials or the panel could be covered in soft materials over a rigid panel portion. The size and shape of the panel would necessarily dictated by the dimension of the electronic device 4.

Figure 3H:
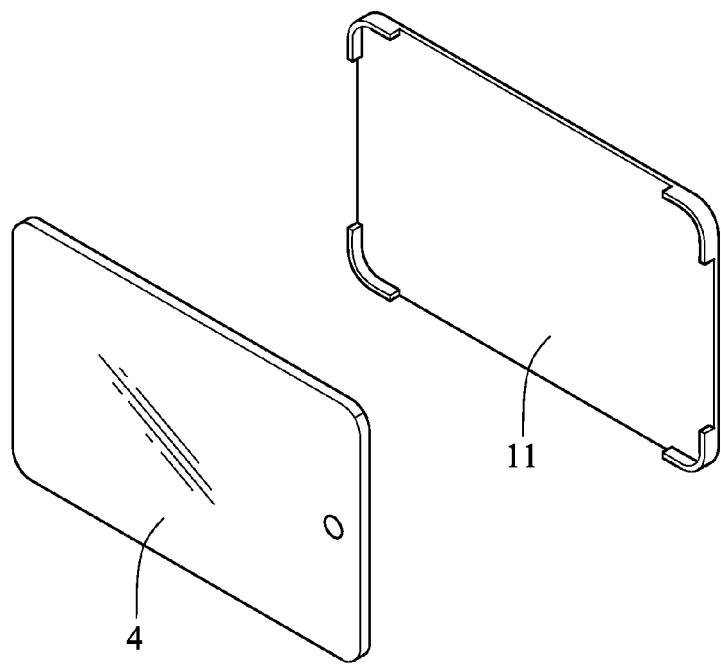
FIG. 3H shows an EMF blocker in the form of a case for the electronic device.

FIG. 3H shows an EMF blocker 2 in the form of a case 11 for the electronic device 4. The blocking shield can consist of the entire case 11, or only portion of the case 11. In a preferred embodiment, the entire case 11 is made of, embedded with, or covered with, EMF blocking material.

Figure 4A:
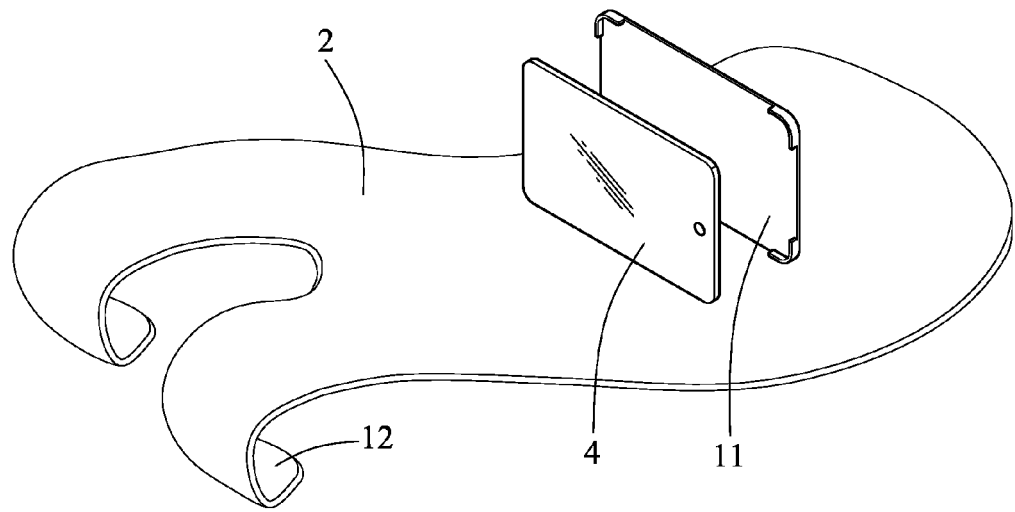
FIG. 4A shows a bib EMF blocker with a detachable case capable of attachment to an electronic device. The detachable case can also detach from the bib.

FIG. 4A shows a bib EMF blocker 2 with a case 11 capable of attachment to an electronic device 4. In this embodiment the case 11 is attached to a medial portion of the EMF blocker 2 with a lower portion available to shield the user's body or legs depending upon how the user is using the device. The upper portion of the EMF blocker 2 is in the shape of a bib with weighted flaps 12 to secure the EMF blocker 2 to the user. The weighted flaps 12 would rest over the user's shoulders. The flaps 12 can or cannot be weighted.

Figure 4B:
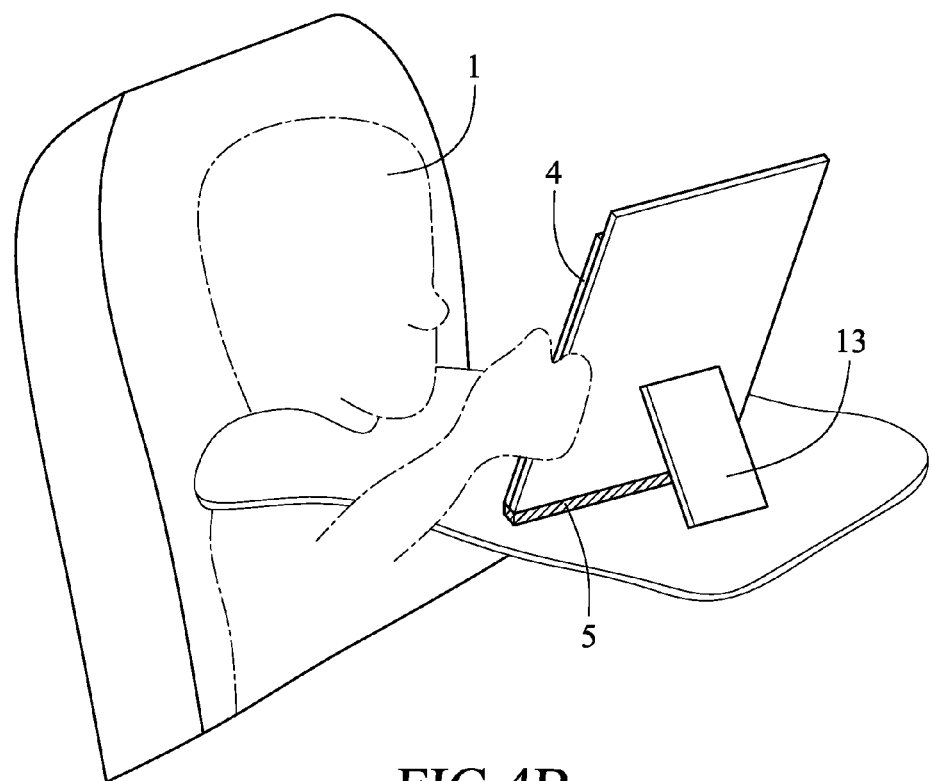
FIG. 4B shows a toddler playing with a tablet PC using the EMF blocker, the tablet PC is attached to a case, which is attached to the bib.

FIG. 4B shows a toddler playing with a tablet personal computer using the EMF blocker 2 on a table. In this configuration, the bib rests over the user's shoulders to protect the user's upper body and the EMF blocker 2 rests underneath the tablet shielding the rest of the user's body. The case 11 is coupled to the bib, having a kickstand 13. In one embodiment, the case 11 is removable from the bib. In other embodiments, the EMF blocker 2 can be attached to the keyboard of a desktop personal computer in a similar manner.

Figure 4C:
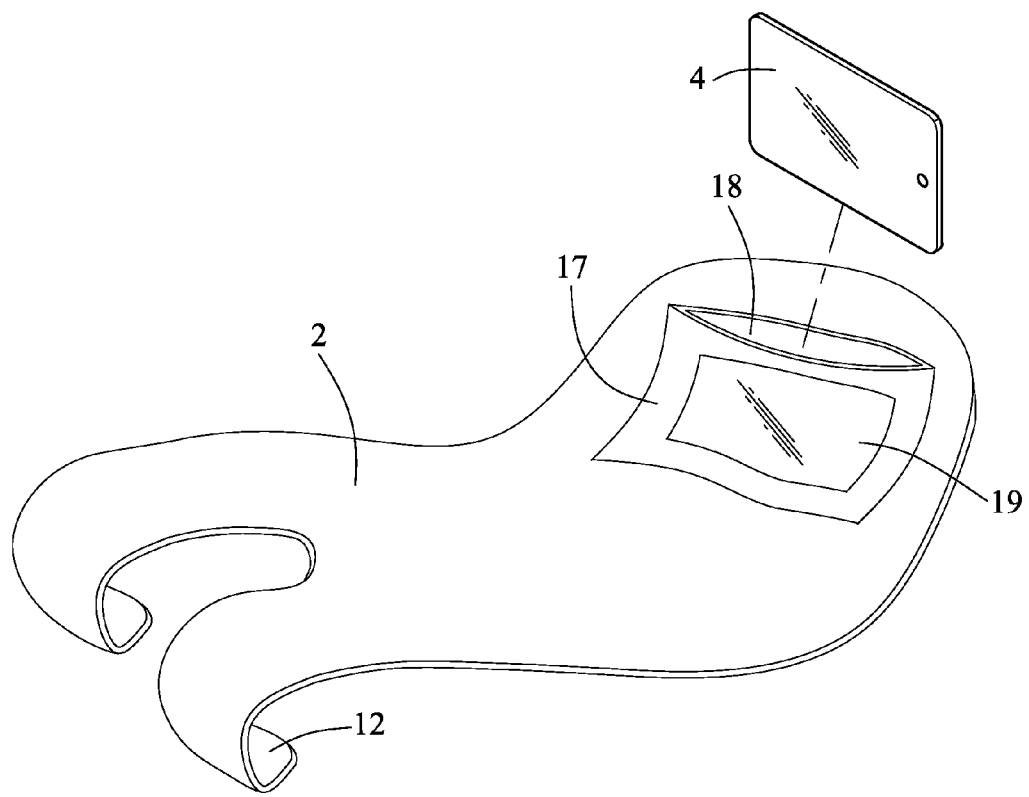
FIG. 4C shows an EMF blocker with a pocket and shoulder flap, and a tablet PC is to be inserted into the pocket through an opening of the pocket. The display screen can be viewed through the transparent window of the pocket.

FIG. 4C shows an EMF blocker 2 with a pocket 17 and shoulder flap 12. The shoulder flap 12 is weighted and helps to frictionally maintain the EMF blocker 2 in place. The pocket 17 has an opening 18 to store an electronic device 4 (e.g., tablet PC as shown). In the case of a device 4 with a touchscreen the user could operate the device through the transparent window 19. In the situation of a device that is just playing back a movie or video the transparent window 19 would allow the user to safely watch the movie.

Figure 4D:
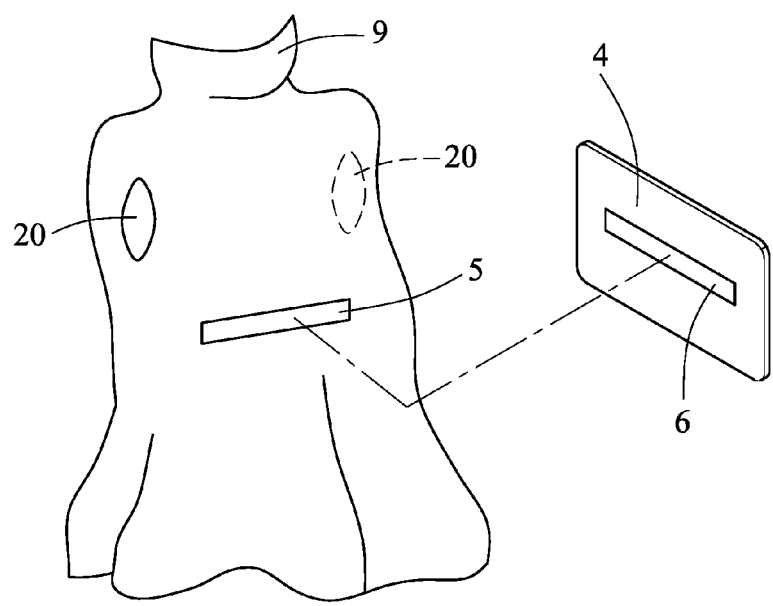
FIG. 4D shows an EMF blocker with a neck guard and sleeve holes with a fastening means for an electronic device.

FIG. 4D shows an EMF blocker 2 with a neck guard 9 and sleeve holes 20 with a coupling means 5 for an electronic device 4. A tablet personal computer is attached with a fastener 6 to the EMF blocker 2. In this configuration the user is secured to the electronic device 4 via the EMF blocker 2 sleeve holes. The user's arms or shoulders support the EMF blocker 2 and the user can be standing, sitting, or lying down. Also, this configuration uses a tall collar 9 to protect the neck and thyroid glands. Because the attachment point for the electronic device 4 is at a medial portion of the EMF blocker 2, this embodiment allows the user to protect the user's upper and lower body, still with the use of just one EMF blocker 2. In this preferred embodiment the upper torso portion of the EMF blocker 2 could have a loop design for slipping over the head while the lower body portion of the EMF blocker 2 could be a simple blanket design to drape over the waist and legs of the user.

Figure 4E:
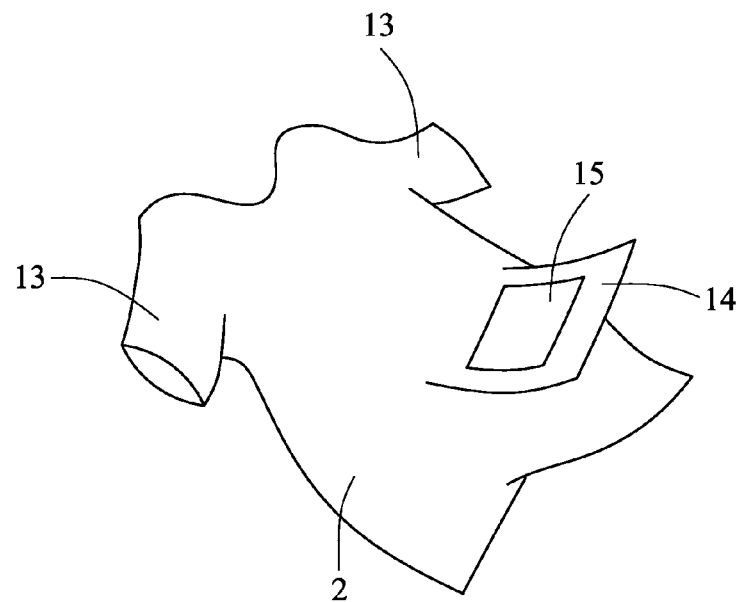
FIG. 4E shows an EMF blocker with sleeves and a flap having material for affixing an electronic device via friction.

FIG. 4E shows an EMF blocker 2 with sleeves and a flap material 14 for affixing an electronic device 4. Additionally, this embodiment has a rubber, thermoplastic elastomer or anti-slip surface 15 incorporated into the flap for use when a user is sitting and has a table or surface to set the flap material. This reduces the chance of the electronic device 4 sliding off the table or surface. The sleeves secure the EMF blocker 2 to the user. Although illustrated here as being used with an embodiment having a flap 14, such method (i.e., using a rubber, TPE, or anti-slip surface) can be used in any contemplated form of EMF blocker.

Figure 4F:
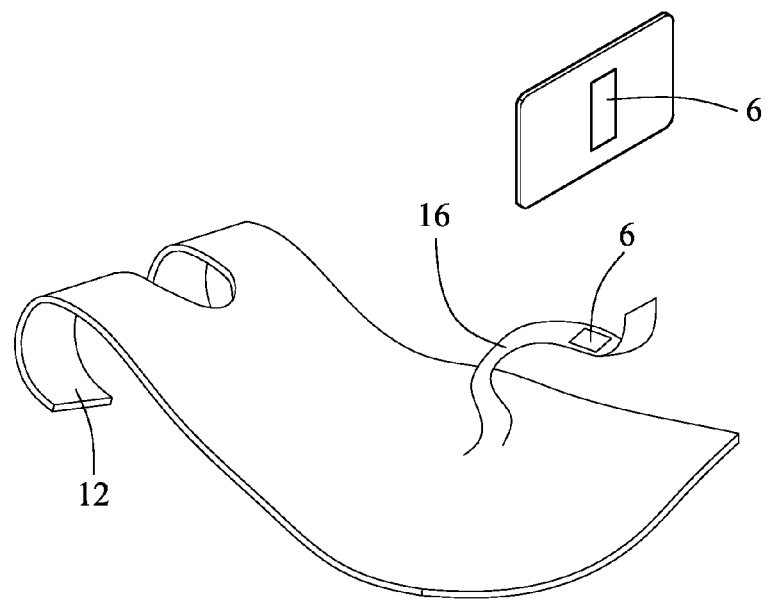
FIG. 4F shows an EMF blocker with an appendage in the form of a strap with a fastener for attaching to an electronic device.

FIG. 4F shows an EMF blocker 2 with an appendage 16 in the form of a strap with a fastener 6 for attaching to an electronic device 4. In this embodiment the EMF blocker 2 can be attached to a user in any of the previously described manners but is shown here with shoulder flaps 12. The fastener 6 at the distal end of the appendage 16 fastens to an electronic device 4. The method of attachment can be the same as disclosed above. The appendage 16 allows the user to freely adjust the electronic device 4 or shift the user's body for comfort. Additionally, if the user is standing or walking the appendage 16 acts as a security device if the electronic device 4 was dropped the appendage 16 would keep the device from hitting the ground. The security feature would limit designs of the appendage 16 to about four or five feet in length and depend on a user's height and the positioning on the EMF blocker 2. This embodiment is also useful for using with a desktop computer where the main CPU is located under the desk. This way, when the appendage 16 is attached to the keyboard on the desk, the bottom portion of the EMF blocker drapes over the user's genital area, protecting the user.

Figure 4G:
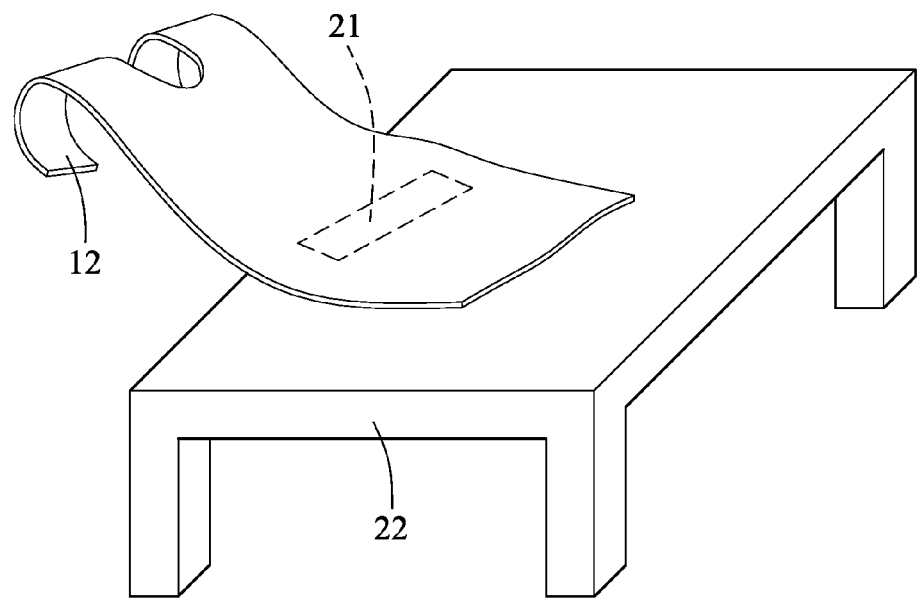
FIG. 4G shows an EMF blocker for placing a desktop PC keyboard, or laptop PC thereon.

FIG. 4G shows an EMF blocker 2 having clear indication instructing a user where to attach or rest a keyboard or laptop, when the EMF blocker is rest on the table 22. In this embodiment the EMF blocker 2 is secured to the user with shoulder flaps 12. The EMF blocker 2 would also have markings at the mid-region of the EMF blocker 2 to rest whatever device on the EMF blocker. In other embodiments, the EMF blocker 2 has additional attachment mechanisms in a medial portion of the EMF blocker 2 to attach to the table 22 so that the user could shift around their body but not disturb the electronic device 4. In the preferred embodiment, the EMF blocker 2 has graphics 21 or instructions printed or otherwise integrated into the surface to aid in folding or attaching or wearing the EMF blocker 2, or aid in resting an electronic device on the EMF blocker 2.

Figure 4H:
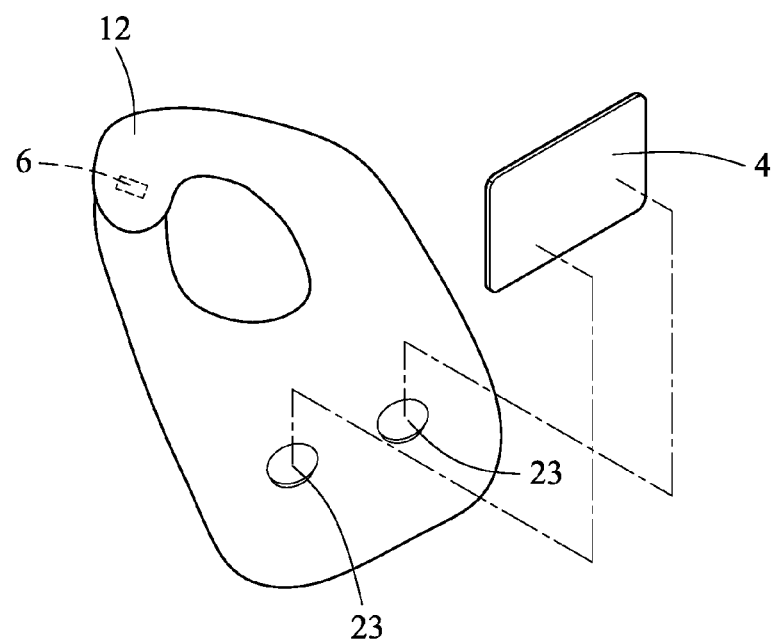
FIG. 4H shows an EMF blocker with a loop design for placement around the user's neck and suction cups for attaching to an electronic device.

FIG. 4H shows an EMF blocker 2 with a loop design with one flap 12 for placement around the user's neck and suction cups 23 for attaching the EMF blocker 2 to an electronic device 4. Also, the embodiment is not limited in the placement of a shoulder flap 12 which could be adjustable. The fastener 6 could be adjusted to accommodate different sized users.

Figure 4I:
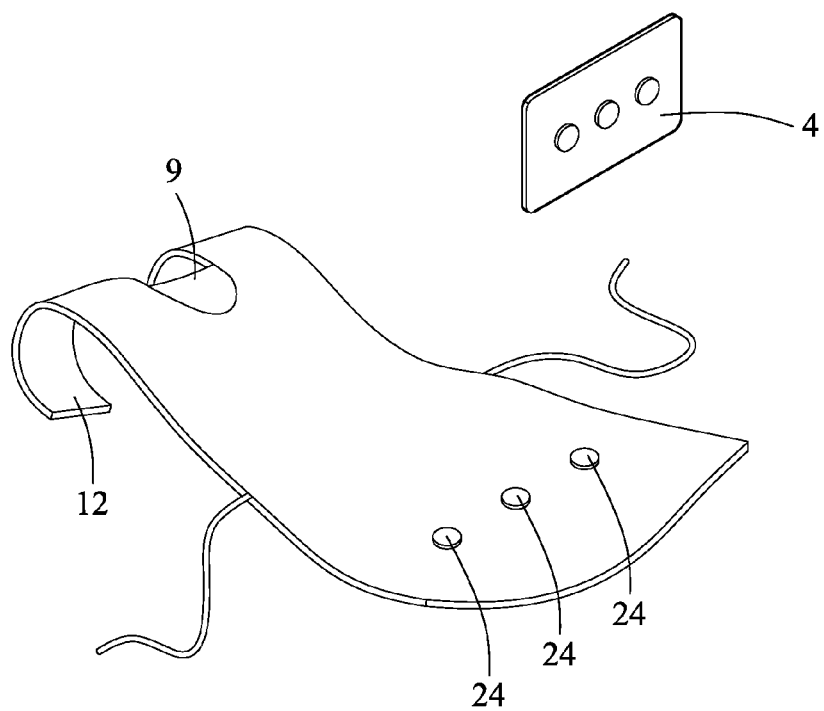
FIG. 4I shows an EMF blocker with a neck guard, shoulder flaps, straps and attachment means of a snap, button, and magnet.

FIG. 4I shows an EMF blocker 2 with a neck guard, shoulder flaps 12, straps 7 and attachment means of a snap, button, and magnet 24. This embodiment shows an EMF blocker 2 with straps 7 that can be tied behind the user's back and is intended for users that use electronic devices 4 for long periods of time. The shoulder flap 12 is comfortable and the neck guard 9 is flared out away from the user to protect the neck area without interfering with the user's ability to turn their head or move around.

Figure 4J:
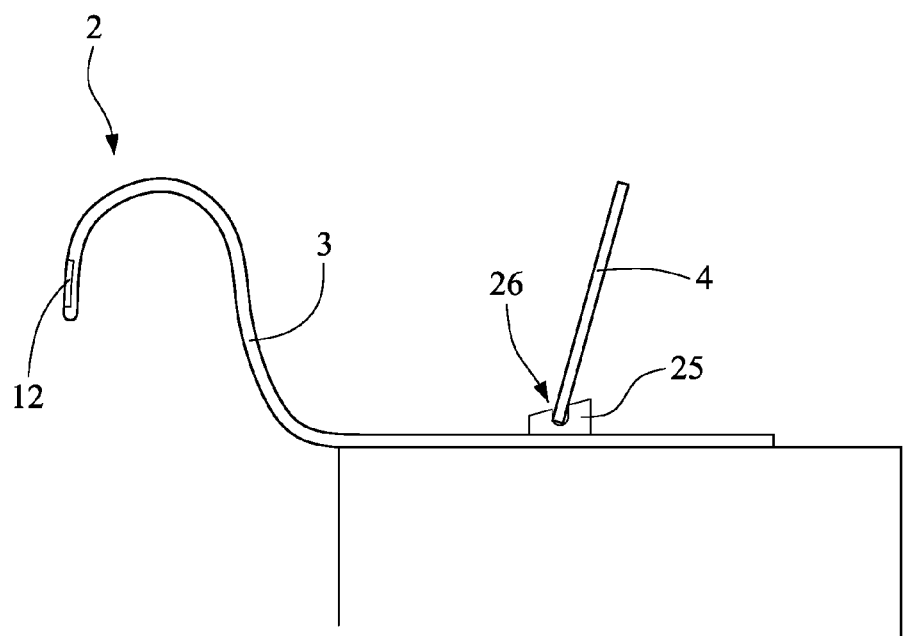
FIG. 4J shows an EMF blocker with a built-in stand for an electronic device.

FIG. 4J shows an EMF blocker 2 with a built in stand 25 for an electronic device 4. In this embodiment the EMF blocker 2 is secured to the user with shoulder flaps 12. The EMF blocker 2 would also have attachment mechanisms at the distal end of the EMF blocker 2 to secure the EMF blocker 2 to a table. The EMF blocker 2 could have additional attachment mechanisms in a medial portion of the EMF blocker 2 to attach to the table so that the user could shift around their body but not disturb the electronic device 4. The stand 25 is incorporated as thin piece of plastic with groove or slit 26 that would allow a user to stably balance an electronic device 4. Additional methods of incorporating a stand 13 into the EMF blocker 2 are known in the arts, such as folding braces or a plastic arm that can rotate from a flush position with the EMF blocker 2 to form a triangular support between the electronic device 4 and EMF blocker 2 like a kickstand.

FIGS. 4A-4J show various ways to fasten an EMF blocker 2 to a person. For example, Velcro®, straps 7, clips, snaps, buttons, loop design (to slip over the head) and sleeves can be used. The various methods have different advantages for different types of users. An adult that may be interrupted frequently may enjoy a hook and loop attachment method because of the ease of detaching and reattaching quickly. Examples of adults that would benefit from this design would be a working parent with small children that need to be tended to frequently. A preferred embodiment is with two clips on the EMF blocker 2. The clip design would work well for older adults that may not have the dexterity to quickly button and un-button a button.

Another preferred embodiment is wherein the EMF blocker 2 can be attached to a user with buttons. The button attachment would work well for a user that is used to working with devices for long durations of time and prefer the robust and firm attachment that buttons can provide. For children, a loop design would be easy to use because it would not require the manual hand dexterity that might be required for attachment with buttons.

Another preferred embodiment wherein the EMF blocker 2 is attached to a user with sleeves. This particular method of attachment is good for users of all age that might not have the dexterity to operate clips or buttons or the strength or flexibility to slip a loop design over their own head.

Figure 5:
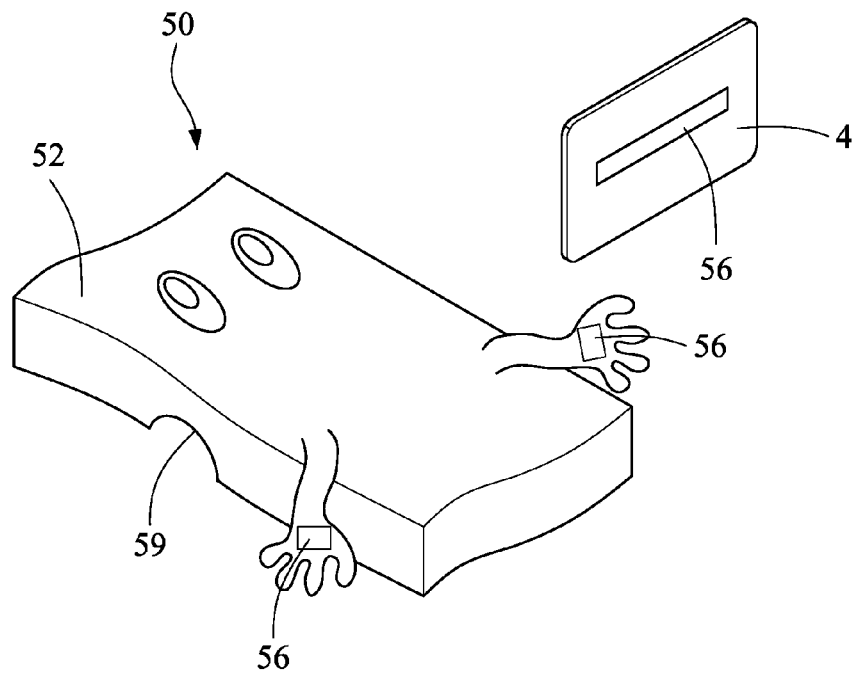
FIG. 5 shows an EMF blocker in the form of a costume with sleeve holes and fasteners attached to the distal end of two appendages.

FIG. 5 shows an EMF blocker 52 in the form of a costume with sleeve holes and fasteners attached to the distal end of an appendage. This embodiment illustrates that the number of appendages and fasteners is not limited to just one. Here the costume provides for two fasteners which can stabilize the electronic device 54 and provide additional protection if a single fastener were to fail. Additionally, it should be understood that the entire costume need not have the blocking shield 3, but only where it would be advantageous such as protecting the reproductive organs or the head and neck.

Figure 6A:
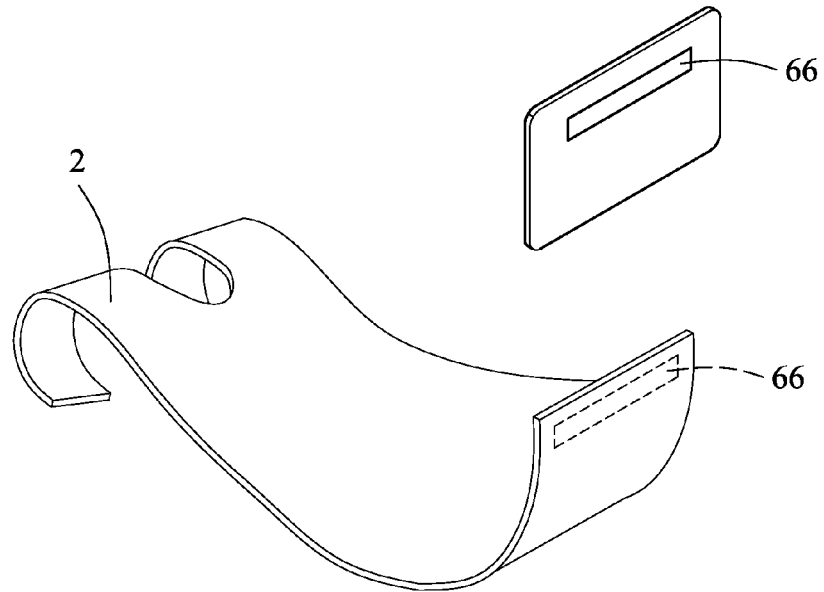
FIG. 6A shows an EMF blocker with VELCRO or hook and loop attachment means at the distal or terminal end of the EMF blocker.

FIG. 6A shows an EMF blocker 2 with VELCRO® or hook and loop attachment means at the distal or terminal end of the EMF blocker 2. VELCRO® or hook and loop is a preferred method of attachment because it is inexpensive, robust, and easy to detach and reattach. This embodiment allows the user to easily place the EMF blocker 2 over the user's body in a single direction. The user could either cover the waist up to the neck and even covering the throat depending on the chosen design or cover the waist down over the legs and feet. This option would be useful for people that had a particular concern, for example a pregnant woman would want to cover her belly and protect her unborn child. Perhaps a user has a family history with a particular type of cancer, thyroid cancer, and therefore would like the option of having a convenient and light weight EMF blocker 2 that could shield the thyroid gland.

Figure 6B:
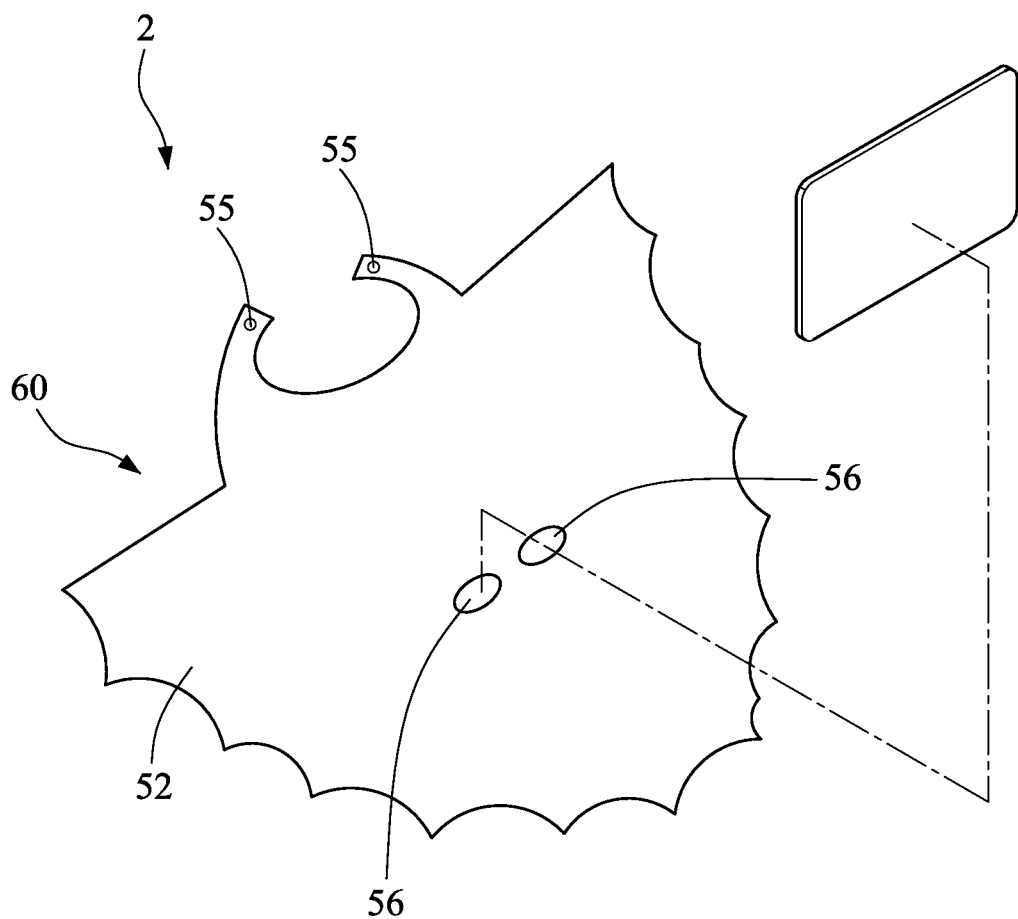
FIG. 6B shows an EMF blocker in the form of a cape with a loop design and magnets to close the loop and fasteners disposed in the mid-region of the blocking shield.

FIG. 6B shows an EMF blocker in the form of a cape 60 with a loop design with two flaps 53 and magnets 55 to close the loop and fasteners disposed in the mid-region of the blocking shield 3. Magnets 55 can be used for affixing two pieces of the EMF blocker 2 around the neck of a user. This particular design is also a costume cape 60 with fasteners 56 disposed in the mid-region of the blocking shield 3. In one embodiment, the EMF blocker 2 is a wearable piece attached to the electronic device or case 11, discussed more below. The wearable piece can be cape-like, and can be worn on the front of a child instead of on the back of the child. Some contemplated embodiments can have sleeves. Other contemplated embodiments can have raised collars just like a vampire's cape so that when the cape is worn on the front of the child, the raised collar protects the child's neck and brain from EMF radiation exposure.

Figure 7A:
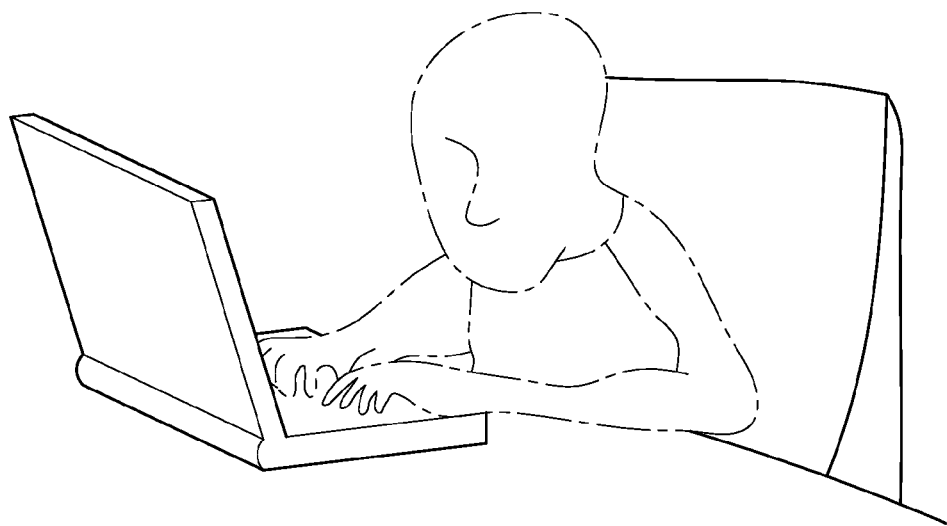
FIG. 7A shows prior art of a user working on a laptop without EMF radiation protection.
Figure 7B:
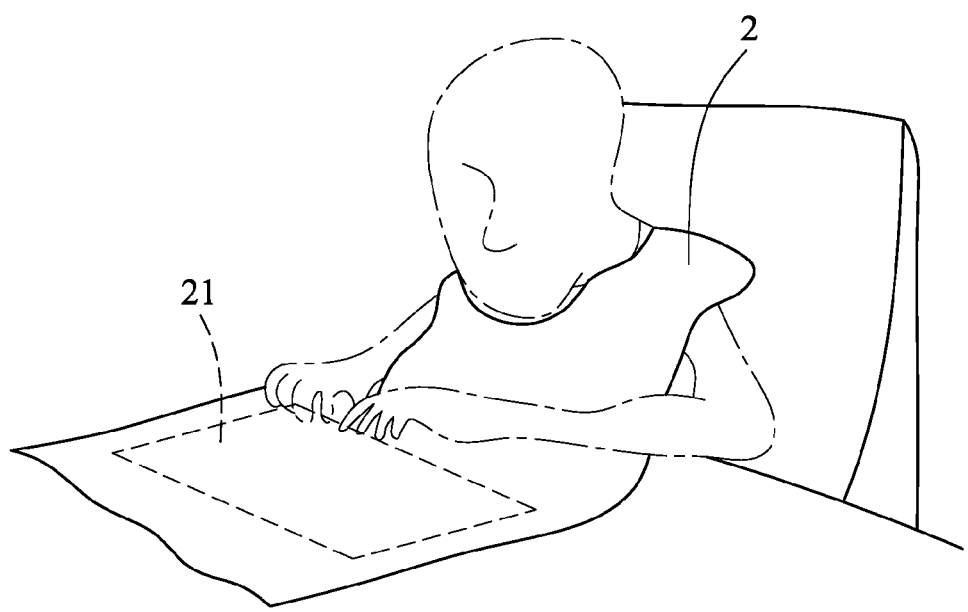
FIG. 7B shows an EMF blocker attached to a user for use, wherein the EMF blocker has clear indication instructing the user where to place the laptop or the keyboard.

FIG. 7A shows prior art of a user working on a laptop without EMF radiation protection. FIG. 7B shows an EMF blocker 2 attached to a user for use with an electronic device on a counter top. The EMF blocker 2 can have markings 21 to show the optimal placement of an electronic device or keyboard on a surface or a coupling mechanism 5. In FIG. 7B, the electronic device is not shown. Although a wired keyboard itself does not emit EMF radiation, the EMF blocker is still suitable for wired keyboard because it uses the keyboard as a guide to tether the desktop PC to the EMF blocker. It is especially contemplated for usage with wireless keyboard, because wireless keyboards are known to emit EMF radiation.

Figure 8:
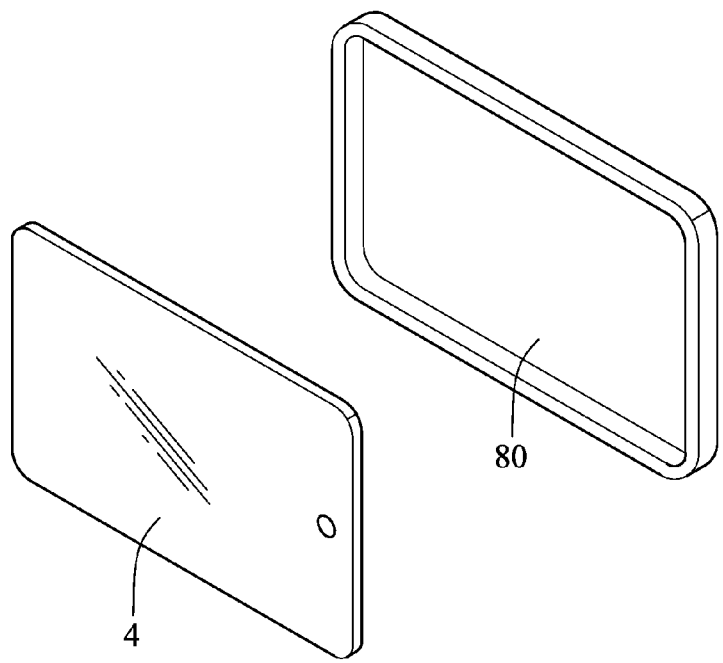
FIG. 8 shows a case with an EMF blocker folded and stored within a pocket of the case.

FIG. 8 shows a case 11 with an EMF blocker 82 folded and stored within a pocket of the case 80. This case 80 is made of EMF blocking material, or have such EMF blocking material as part of the case 80. Specifically, there are different materials that are commercially available such as Silverell™ and ARGENTEX™ which are manufactured with proprietary methods and discussed in greater detail below. The cover and the EMF blocker 82 fold nicely together. Optionally, the EMF blocker can be detached from the cover before the cover is closed on the electronic device 4. Many other folding and unfolding configurations are contemplated, such as the way any of the known diaper changing mats are known to be folded and unfolded. The method of attachment of the EMF blocker 82 to the hard cover could be by use of VELCRO (hook and loop) material, snaps, zipper, or buttons. In an alternative embodiment the EMF blocker could be attached directly to the electronic device 4 using VELCRO (hook and loop) material, snaps, or tensioned loop material (like a rubber band or bungee cord).

In one embodiment, the EMF blocker 2 is partially and directly attached to the bottom side of the electronic device 4 without the need for a hard or soft cover. In yet another embodiment, a hard or soft cover is present, and the hard or soft cover also acts as an EMF blocker 2, by having the necessary EMF-blocking material as part of the soft or hard cover to protect a user, more specifically reproductive organs, from EMF radiation exposure.

In a preferred embodiment an EMF blocker 2 can be attached to the electronic device 4 or case with snaps 24. This embodiment allows a robust attachment that is easy to detach as well. Although, having to permanently attach a snap receptacle to an electronic device 4 may not be user friendly. An alternative embodiment wherein an EMF blocker 2 can be attached to the case with a zipper. EMF blocker 2 can be washable and the ability to remove it from the case would probably be required unless the case 11 was also made of washable materials.

In a preferred embodiment an EMF blocker 2 can be attached to a case 11 with buttons 24. The button attachment embodiment is very preferable because it provides a stable platform for further attaching the EMF blocker 2 to a user.

A preferred embodiment wherein an EMF blocker 2 can be attached to a case 11 and where a pocket is formed in the case 11. For example, the pocket could be in a medial portion of a towel shaped and sized EMF blocker 2. The electronic device 4 could be placed in the pocket and the towel shaped and sized EMF blocker 2 could be rolled up for storage and rolled out for use. Also, the EMF blocker 2 can be simply a lap blanket. Further, the EMF blocker can be in a form of a Snuggie® sleeved blanket. In yet another embodiment the EMF blocker 2 can be attached to either an electronic device 4 or a case 11 and the EMF blocker 2 is in the shape of a sleeve. The EMF blocker 2 can be in the shape of any article of clothing to be worn by a human or pet.

In yet another embodiment, a cover can have a pocket for the EMF blocker 82 to be stowed away. The pocket can be open or resealable. The pocket with the resealable form can utilize a zipper, buttons, snaps, or Velcro to seal the pocket closed. Alternatively, the EMF blocker 82 can be attached inside the pocket and act as an anchor for spreading out the EMF blocker 82, in this embodiment of the invention the method of attachment is in the form of a zipper, buttons, snaps or Velcro. An alternative embodiment wherein a case 11 is made of a soft material. A soft material can include or be entirely made from synthetic material such as neoprene, perforated foam or preformed foam. One skilled in the art would recognize the many possibilities available to make the case 11.

Figure 9:
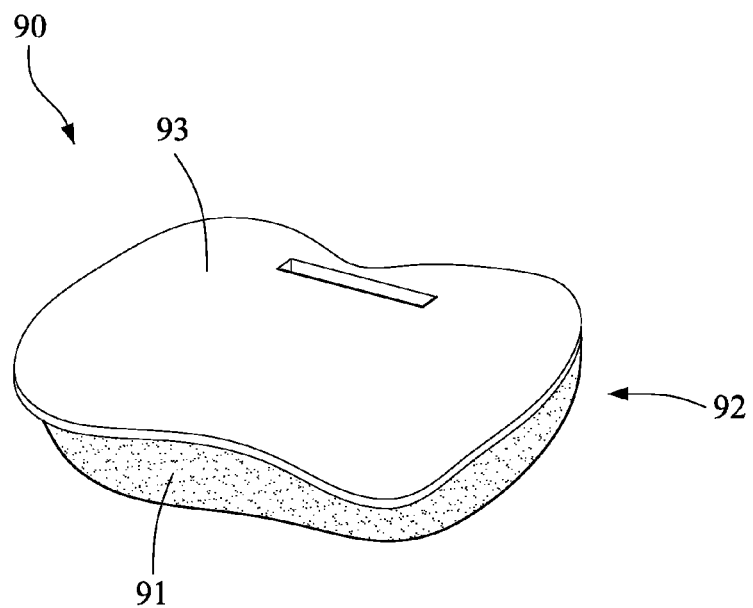
FIG. 9 shows a preferred embodiment where EMF blocker is in the form of a laptop pillow table with a hard surface, and the blocking shield is stored within the pillow.

FIG. 9 shows a preferred embodiment where EMF blocker 92 is in the form of a laptop pillow table 90 with a pillow 91 and hard surface 93.

In a preferred embodiment, the contemplated EMF blocking material is a yarn fiber/fabric substrate with a silver layer on them, where the silver layer is 99.9% pure and permanently bonded to the surface of the textile in a unique metallizing process that bonds silver on polyamide based materials.

The EMF blocker is in the preferred form of a thin fabric. EMF blocker can be made of the above listed materials together with any soft, pliable material could be used, such as silk material, leather material, neoprene material, Lycra® material, Rayon material, Acetate material, Nylon material, Modacrylic material, Polyester material, Polylactide material, Vinyon material, Spandex material, Lyocell material, Acrylonitrile rubber material, plastic material, and/or polyester material, and blends thereof. The material can be made with electromagnetic radiation blocking material such as silver, copper, gold, aluminum, iron, steel, brass, bronze, nickel, zinc, tungsten, platinum, molybdenum, chromium, titanium, manganese, graphite and other carbon-based compounds, polymers, ceramics, plastics, and alloys or composites thereof. Various methods of treating the material include spraying, dipping, or coating material in bulk after manufacturing. Also, as in the preferred embodiments above, the radiation blocking material could be incorporated into the base polymers prior to weaving the EMF blocker material.

In addition, the same idea can be expanded to protect people, children, toddlers, and infants traveling on airplanes from the airplane's EMF exposure by providing a cape, a dress, a towel, a shirt, or some type of covering to wrap at least a part of the person's body. In a preferred embodiment the EMF Blocker would be shaped to form a high collar 9 to protect the throat and neck of a user. Although the drawing figures do not show an adult using the contemplated device, it should be recognized that this invention is also intended for adults, even family pets.

The EMF blocker as shown in the figures are in the forms of fabric sheets and blankets. It is also contemplated to have the EMF blocker made in the form of hard panels similar to the bottom plate as shown in FIG. 3G. Suitable materials are known in the industry such as low-resilience polyurethane which is light weight and impact resilient.

Such EMF blocking material may also be sprayed on. One skilled in the art would recognize various different possible ways to incorporate such EMF blocking material.

Also, one skilled in the art would recognize the many other types of material can be used so long as they provide the same or similar functionalities.

For the sake of clarity the fasteners and attachment means are described throughout but should also include the following a suction cup, a button, a clip, a snap, a hook-and-loop fastener, a magnet, an elastic band, a receiving slot to receive and keep the electronic device 4 at an angle, a flip up frame kickstand, and a material to secure the electronic device 4 in place by friction.

For the sake of clarity the fasteners and attachment means and coupling mechanism 5 are described throughout but should also include the following a suction cup, a button, a clip, a snap, a hook-and-loop fastener, a magnet, an elastic band, a receiving slot to receive and keep the electronic device 4 at an angle, a flip up frame kickstand, and a material to secure the electronic device 4 in place by friction.

It will be understood that various modifications can be made to the various embodiments of the present invention herein disclosed without departing from the spirit and scope thereof. For example, various devices are contemplated as well as various types of construction materials. Also, various modifications may be made in the configuration of the parts and their interaction. Therefore, the above description should not be construed as limiting the invention, but merely as an exemplification of preferred embodiments thereof. Those of skill in the art will envision other modifications within the scope and spirit of the present invention as defined by the claims appended hereto.

What is claimed is:

1. An accessory to an electronic device, wherein the electronic device is a cellular phone, a tablet computer, a laptop computer, a portable DVD player, a portable video game player, or a desktop computer, and wherein the accessory detachably attaches to the electronic device and minimizes impact of electromagnetic field (EMF) radiation to a user emitted from the electronic device, the accessory comprising:
   a blocking shield detachably coupled to the electronic device allowing a user to use the electronic device while the electronic device is attached to the blocking shield;
   wherein the blocking shield is in a form of at least one selected from a group consisting of a blanket, an article of clothing, a bib, an apron, a panel, a case; and
   wherein a EMF radiation-blocking material is embedded in at least part of the blocking shield;
   wherein the blocking shield is at least one of a blanket, an article of clothing, a bib, an apron, and a panel made of soft fabric-like material, and the blocking shield is coupled to the electronic device via a coupling mechanism;
   wherein the coupling mechanism is at least one of a fastener, a strap, and a case in the blocking shield.

2. The accessory as recited in claim 1, wherein the blocking shield is coupled to the electronic device via a fastener, wherein the fastener is coupled to the blocking shield and is at least one selected from a group consisting of a suction cup, a button, a clip, a snap, a hook-and-loop fastener, a magnet, an elastic band, a receiving slot to receive and keep the electronic device at an angle, a flip up frame kickstand, and a material to secure the electronic device in place by friction.

3. The accessory as recited in claim 2, wherein the blocking shield is sufficiently long to cover the user's shoulders and genital area.

4. The accessory as recited in claim 2, further comprising a neck guard as part of the blocking shield, to sufficiently cover at least a front part of the user's neck, when the blocking shield is also covering over the user's shoulders.

5. The accessory as recited in claim 4, wherein the article of clothing is a reverse cape, a costume.

6. The accessory as recited in claim 1, wherein the blocking shield attaches to the user via at least one of a wearable sleeve, a strap, and a weighted flap.

7. The accessory as recited in claim 6, wherein the coupling mechanism is disposed at a mid-region of the blocking shield.

8. The accessory as recited in claim 6, wherein the blocking shield is sufficiently long to cover both the user's shoulders and genital region.

9. The accessory as recited in claim 1, wherein the electronic device is a mobile electronic device, and wherein the blocking shield is coupled to the mobile electronic device via the case, the case encloses at least a part of the mobile electronic device, and the case is detachably attached to the blocking shield.

10. The accessory as recited in claim 1, wherein the electronic device is a mobile electronic device, and wherein the blocking shield is a case, the case encloses at least a part of the mobile electronic device.

* * * * *